(12) United States Patent
Hellenkamp

(10) Patent No.: US 6,387,107 B1
(45) Date of Patent: *May 14, 2002

(54) POSITIONING ASSEMBLY FOR RETAINING AND POSITIONING A CORNEA

(76) Inventor: Johann F. Hellenkamp, 10060 SW. 89th Ct., Miami, FL (US) 33176

( * ) Notice: Subject to any disclaimer, the term of this patent is extended or adjusted under 35 U.S.C. 154(b) by 0 days.

This patent is subject to a terminal disclaimer.

(21) Appl. No.: 09/518,453

(22) Filed: Mar. 3, 2000

Related U.S. Application Data

(63) Continuation of application No. 09/107,793, filed on Jun. 30, 1998, now Pat. No. 6,042,594, which is a continuation of application No. 08/741,955, filed on Oct. 31, 1996, now Pat. No. 5,772,675.

(51) Int. Cl.$^7$ ............................................. A61B 17/00
(52) U.S. Cl. ...................................................... 606/166
(58) Field of Search ........................... 606/1, 4, 5, 107, 606/161, 166, 167; 604/294; 600/387, 208, 236

(56) References Cited

U.S. PATENT DOCUMENTS

| | | | |
|---|---|---|---|
| 3,074,407 A | * | 1/1963 | Moon et al. |
| 4,688,570 A | * | 8/1987 | Kramer et al. |
| 5,009,660 A | * | 4/1991 | Clapham |
| 5,092,863 A | * | 3/1992 | Schanzlin |
| 5,489,299 A | * | 2/1996 | Schachar |
| 6,042,594 A | * | 3/2000 | Hellenkamp |

* cited by examiner

Primary Examiner—Henry J. Recla
Assistant Examiner—W. Lewis
(74) Attorney, Agent, or Firm—Malloy & Malloy, P.A.

(57) ABSTRACT

An improved positioning assembly for positioning a cornea of an eye during surgery includes a positioning element, a suction force operably coupled to the positioning element to temporarily attach it to the eye, and a suction enhancement assembly. The positioning element includes a retention plate, having an aperture defined therein to receive the cornea of the eye for engagement with an interior rim disposed in surrounding relation about the aperture, and a flange member extending downwardly from the retention plate in spaced, surrounding relation to the aperture. The positioning element further includes a vacuum port in fluid flow communication with a point radially exterior of the aperture such that a suction force applied therethrough secures the positioning segment to the eye with the cornea protruding through the aperture. The suction enhancement assembly preferably includes a resilient material segment structured to engage the positioning element at a point radially exterior of the aperture, and disposed to define a suction channel between the suction enhancement member and the positioning element, which channel is in fluid flow communication with the vacuum port. A plurality of suction ports are preferably defined in the segment and improve the vacuum seal about the eye. The suction enhancement assembly promoting suction, while affirmatively preventing partial or complete occlusion thereof.

18 Claims, 2 Drawing Sheets

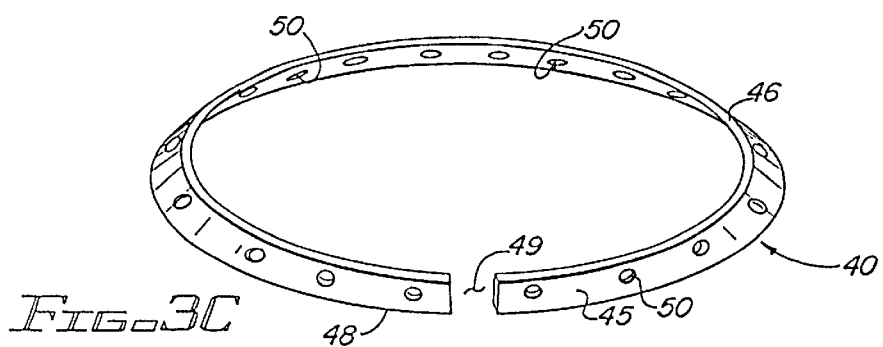
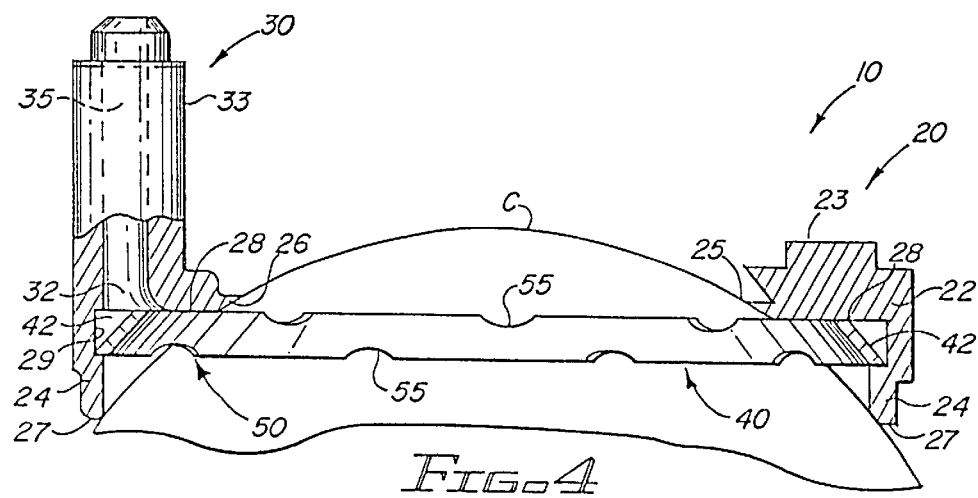
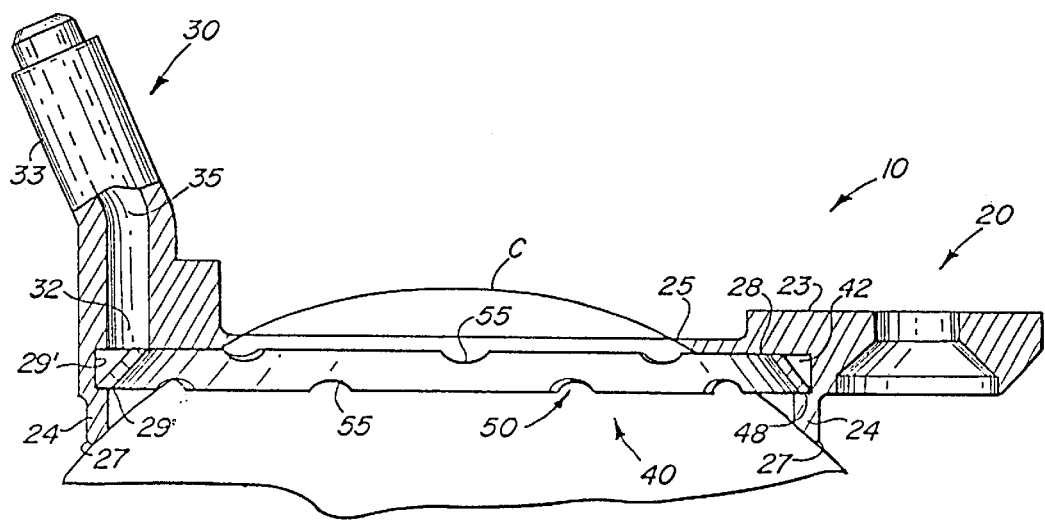

POSITIONING ASSEMBLY FOR RETAINING AND POSITIONING A CORNEA

CLAIM OF PRIORITY

The present is a Continuation of pending U.S. patent application Ser. No. 09/107,793, filed on Jun. 30, 1998, which issued as U.S. Pat. No. 6,042,594 which is a Continuation of U.S. patent application Ser. No. 08/741,955, filed Oct. 31, 1996, which issued as U.S. Pat. No. 5,772,675 on Jun. 30, 1998.

BACKGROUND OF THE INVENTION

1. Field of the Invention

The present invention relates generally to a medical apparatus used during the performance of eye surgery and in particular, is directed towards a positioning assembly for retaining and positioning a patient's eye for cutting of the cornea during a surgical procedure, such as to correct for refractive error. More specifically, the present invention is specifically directed to achieving and maintaining an improved attachment of a positioning element to the eyeball during surgery.

2. Description of the Related Art

The eye works on a principle very similar to that of a camera wherein the iris, or colored portion of the eye about the pupil, functions like a shutter to regulate the amount of light admitted to the interior of the eye. The cornea or clear window of the eye, and the lens, which is located behind the pupil, serve to focus the light rays from an object being viewed onto the retina at the back of the eye. The retina then transmits the image of the object viewed to the brain via the optic nerve. Normally, these light rays will be focused exactly on the retina, which permits the distant object to be seen distinctly and clearly. Deviations from the normal shape of the corneal surface however, produce errors of refraction in the visual process so that the eye becomes unable to focus the image of the distant object on the retina, with the result that one sees a blurred image.

About twenty years ago, such refractive errors could only be treated with eyeglasses or contact lens, both of which have well known disadvantages for the user. Since then, however, surgical operations have been developed to change the refractive condition of the eye. Several methods and special instruments have been designed for performing this kind of surgery, which are primarily directed to reshape the cornea. It will be appreciated that the goal of corneal reshaping is to modify the curvature of the cornea, i.e., either to flatten or increase its curvature depending on the patient's condition, so that light rays passing through the cornea will thereafter be refracted to focus or converge directly onto the retina, thereby permitting the patient to view a distant object clearly.

One such surgical operation is keratomileusis, which requires a precise reshaping of the cornea by cutting and separating a thin layer of corneal tissue, termed the corneal cap, by lathing that tissue and then, by suturing the reshaped corneal tissue back into place on the eye. Keratomileusis is viewed, however, as having several drawbacks, and consequently, has been abandoned in recent years. Automated Lamellar Keratectomy (ALK) is another surgical technique which developed as an outgrowth of keratomileusis. In an ALK procedure, the eye is typically first numbed by a drop of anesthetic, and then, a device having a ring shaped configuration is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the ring shaped device to cut into the cornea. Under an ALK procedure to treat near-sightedness, the microkeratome is typically first used to cut and lift a thin layer of the cornea, instead of severing it, and second, to carry out a reshaping of the cornea by way of a second pass of the microkeratome over the cornea with the cutting element adjusted to pass therethrough at a desired and pre-determined corrective depth. Thereupon the thin, raised layer of corneal tissue is put back in place over the cornea for healing. Despite developments in the art utilizing a laser to carry out the step of re-shaping the cornea, the above-described ALK procedure for near-sightedness may still be followed in certain cases, depending on the depth of the corneal cut needed. Conversely, ALK procedures to treat far-sightedness, wherein the microkeratome is used to make a single cut, are generally no longer followed given the advances which have since occurred in the field.

From the foregoing, it will be appreciated that ALK procedures are considered to possess drawbacks, particularly in that the penetration of the microkeratome's cutting element into the cornea to a precise depth is critical and may not always be achieved. Thus, in more recent years, substantial advances have been made for correcting refractive errors of the eye utilizing a laser to reshape the cornea. One such procedure, known as Laser Intrastromal Keratomileusis, (LASIK), is currently considered optimal because it allows sculpting of the cornea without damaging adjacent tissues, and further, because with the aid of computers, the laser can be programmed by a surgeon to more precisely control the amount of tissue removed, and significantly, to permit more options for the reshaping of the cornea. Under LASIK procedures, the eye is still typically positioned within a ring shaped device and a microkeratome is typically first used to cut into the cornea so as to raise a thin layer of the cornea, prior to treatment with the laser to reshape the cornea. Still, however, and regardless of the procedure employed, great care and precision are of critical importance to the safety and success of the procedure.

The use of a device having a ring shaped configuration to hold the eyeball in place during a corneal reshaping surgery is well known in the art. Such devices are commonly attached to the eyeball temporarily by way of a suctioning force or vacuum. A typical suction ring device is depicted in FIG. 1 and is seen to include an annular, hollow ring, R, defining an aperture, A, which allows the cornea to be exposed, and an open bottom side that is applied to the surface of the eyeball around the cornea. The ring, R is seen to be in communication with a hollow suction tube, T which opens into the hollow open bottom side of the ring. Commonly known suction ring devices apply a vacuum to the ring R, via tube T, to the eyeball at a single point, P, illustrated in FIG. 2. When the suction ring is applied to the eyeball, with suction or a vacuum applied to the hollow tube, and thus, to the bottom of the ring, the suction ring attaches to the surface of the eyeball surrounding the cornea, with the suction force holding the ring in a reasonably secure fashion, to the eyeball. As a result, the suction ring has become a conventional device in ophthalmic practice, and it should be noted, is designed to be re-usable so as to accommodate a large number of patients over the course of its useful life.

Ophthalmologists have complained, however, that during surgery the vacuum seal, which attaches the suction ring device to the eyeball, may break on occasion. Although not a common occurrence, when the vacuum seal breaks, it is extremely serious in that the precise positioning or centration of the suction ring on the eyeball is lost. More specifically, a critical first step in performing corneal reshaping surgery is the accurate centration of the suction ring on the eye, in precise alignment with the optical axis, with the suctioning force applied to achieve a reliable vacuum seal to maintain the eyeball in the centrated position. If surgery on the eye is underway, with reshaping of the cornea in progress, and the vacuum seal breaks, there can be devastating consequences. Consequently, it is considered imperative that any cutting of the cornea be stopped immediately. Moreover, surgery on the eye should not resume as quite obviously, it is not feasible for the suction ring to be precisely re-aligned or re-centrated in its original position, and it is even more improbable that the cutting element can be precisely re-aligned with the cutting of the cornea already underway. Surgery in progress should therefore be stopped, and any cut portions of the cornea should be returned to a proper position on the eye, with the eye being permitted to heal over the course of three months, before surgery on that eye can be undertaken anew. It will therefore be appreciated that this situation is utterly undesirable for several reasons, but primarily because of the potentially devastating consequences to the patient.

One known factor which contributes to the occasional breakage of the vacuum seal attaching the suction ring to the eyeball is the partial or complete occlusion of the suction force being applied. Specifically, when a vacuum is applied to known suction ring devices during surgery, the vacuum necessarily acts on tissue about the eyeball and more particularly, a mucous membrane that lines the exposed surface of the eyeball known as conjunctiva. With many patients, this factor does not affect the surgery. Other patients, however, have a condition is generally known in the art as "chemosis" which can affect the surgery. Chemosis is a condition wherein fluids can exist under the conjunctiva of the eye such that during surgery, the action of the vacuum on the conjunctiva can cause it to pull away from the surface of the eyeball and towards the single vacuum focal point P of the suction ring. When this occurs, the vacuum can become completely or partially blocked, with the result that the vacuum seal is compromised and likely, broken. It will be recognized that the patient condition of chemosis is relatively uncommon and generally, will be detected before cutting of the cornea begins, and in that case, there is no untoward consequence for the patient. The concern for serious complications arises when surgical cutting of the cornea is underway at the time the vacuum seal breaks, such as by the effects of chemosis, explained above.

Another factor may also contribute to the occasional breakage of the vacuum seal which attaches the suction ring to the eyeball during surgery. Specifically, during surgery the action of the suction force may draw some mucus from the eye into the internal passages of the vacuum, such as into the hollow tube T, shown in FIGS. 1 and 2. Should this occur, it is unlikely to lead immediately to the occlusion of the vacuum. On the other hand, an effective cleaning of the suction ring's internal vacuum passages is tedious at best, and at worst, may not truly be possible. Consequently, any mucus which is drawn into the vacuum passages of the suction ring may remain there to harden in place. Over time then, it is possible for mucus to build-up and accumulate within the internal vacuum passages of a suction ring. A partial or complete occlusion of the suction force applied to the suction ring might eventually result during a subsequent surgery, and lead to a breakage of the vacuum seal.

A potential solution to the problem might be to apply the vacuum to known suction ring devices at more than a single vacuum point on the suction ring. However, the action of a suction force applied to the suction ring, even through a plurality of vacuum points thereabout, might still cause chemosis in that conjunctiva could still block one or more of the vacuum points. This is particularly true in that the suction force applied to the suction ring would likely remain un-dispersed and concentrated at the vacuum points. Additionally, the problem would persist of eye mucus becoming lodged within the interior vacuum passages of the suction ring. As has been described, a thorough cleaning of the suction ring's internal vacuum passages may not be possible, and even if it were possible, cleaning mucus out of the internal vacuum passages would be time consuming. This factor alone carries a negative economic impact in that only a smaller number of surgeries could be performed with the device in a single day.

Therefore, there remains a need in the art for a positioning assembly which not only retains and positions a cornea of patient's eye during surgery, but which has an improved ability to remain securely attached to the eyeball during surgery, without occlusion of the vacuum. Any such improved positioning assembly should be capable of functioning with known suction rings. It would be highly beneficial if any such improved positioning assembly were able to enhance the suction gripping ability of the suction ring device so as to offer a seal about the eye which is more resistant to being broken during surgery. Any such suction enhancement assembly would preferably provide a suction force substantially about the girth of the eyeball, if not entirely thereabout, instead of to a single point adjacent the eyeball, and further, would be structured to apply the suction force about the eyeball in a dispersed and uniform manner. Any such suction enhancement assembly would ideally prevent the effects of chemosis, that is, prevent conjunctiva from partially or completely blocking the suctioning force applied to the suction ring, and further, would ideally limit, if not prevent altogether, eye mucus from entering the interior vacuum passages of the suction ring during surgery.

SUMMARY OF THE INVENTION

The present invention is designed to satisfy the needs which remain in the art and is directed towards a positioning assembly for retaining and positioning a cornea of patientts eye for performance of a surgical procedure thereon. More specifically, the present invention is directed towards improving and preserving the vacuum seal between a suction ring, also known as a positioning ring or positioning element, and an eyeball to which the ring is attached during surgery. While the present invention has application to any eye, it would typically be used on the human eye.

The positioning assembly of the present invention is seen to comprise suction enhancement assembly for use with a positioning element or segment, typically a generally circular positioning ring, and a suctioning assembly operably coupled thereto. More specifically, the positioning assembly may include a positioning segment having a main body, which defines an aperture sized to receive and expose the cornea to be cut and which preferably includes a flange member extending downwardly therefrom and generally about the aperture so as to define a generally open bottom side. The assembly may also comprise a suctioning assembly operably coupled to the positioning segment for supplying a suction force to an undersurface thereof to temporarily attach the positioning segment to a portion of the eye surrounding the cornea to be cut during surgery. The suction enhancement assembly of the present invention is preferably structured and disposed to enhance engagement substantially about the entire aperture of the positioning segment and further, preferably defines, at least partially between the suctioning assembly of the positioning segment and the portion of the eye surrounding the cornea to be cut, a suction channel. The suction enhancement assembly is additionally structured and disposed such that the suction channel is maintained generally free from chemosis and other mucous tissue, which might otherwise completely or partially block the suction force applied through the positioning segment.

An object of the present invention is to provide a positioning assembly having an improved ability to prevent the vacuum seal, which attaches a positioning segment to the cornea of a patient's eye in a precisely controlled orientation for cutting during surgery, from being broken.

It is also an object of the present invention is to provide a positioning assembly which enhances the suction gripping ability of a positioning segment so as to more securely and more uniformly attach the positioning segment to an eyeball once a vacuum or suctioning force is applied during surgery.

Another object of the present invention is to provide a positioning assembly having suction enhancement structure disposed substantially about the eyeball so as to evenly distribute the suction force about the eyeball and thereby, offer a more secure and more stable attachment to the eyeball during surgery.

An additional object of the present invention to provide a positioning assembly having a suction enhancement assembly structured and disposed to define a suction channel between the suctioning assembly and the eyeball to be cut during surgery, and further, to maintain the suction channel evacuated even in the presence of chemosis and/or mucous tissue which might otherwise effect an occlusion of the suction force being applied to the assembly.

An advantage of the present invention is that it offers a positioning assembly having an improved seal about the eye when a suctioning force is applied, which seal is highly resistant to being broken during surgery on the eye.

A feature of the suction enhancement assembly according to the present invention is the ability to be utilized with known suction ring devices.

Yet another object of the present invention is to provide a positioning assembly having suction enhancing structure which can be easily introduced into, as well as removed from, the positioning segment for disposal, without damaging the positioning segment.

Another advantage of the present invention is that in offering a removable suction enhancement member, it facilitates cleaning of the positioning segment.

Yet another advantage of the present invention is that the amount of time required to properly clean the positioning segment is reduced, thereby allowing a surgeon to use the positioning segment to perform a larger number of surgical procedures in a single day.

These and other objects, features and advantages of the present invention will become more readily apparent from the drawings and the detailed description which follows.

BRIEF DESCRIPTION OF THE DRAWINGS

For a fuller understanding of the nature of the present invention, reference should be had to the following detailed description taken in connection with the accompanying drawings in which:

FIG. 3-B is a front view of the suction enhancement assembly of the present invention in an alternative embodiment;

FIG. 3-C is a front view of the suction enhancement assembly of the present invention in yet another alternative embodiment;

FIG. 4 is a partial cross sectional view of the improved positioning assembly according to one embodiment of the present invention and illustrated in an operative position about an eyeball with a suction force applied thereto; and FIG. 5 is a partial cross sectional view of the improved positioning assembly according to another embodiment of the present invention and illustrated in an operative position about an eyeball with a suction force applied thereto.

Like reference numerals refer to like parts throughout the several views of the drawings.

DETAILED DESCRIPTION OF THE PREFERRED EMBODIMENT

Figure 1:
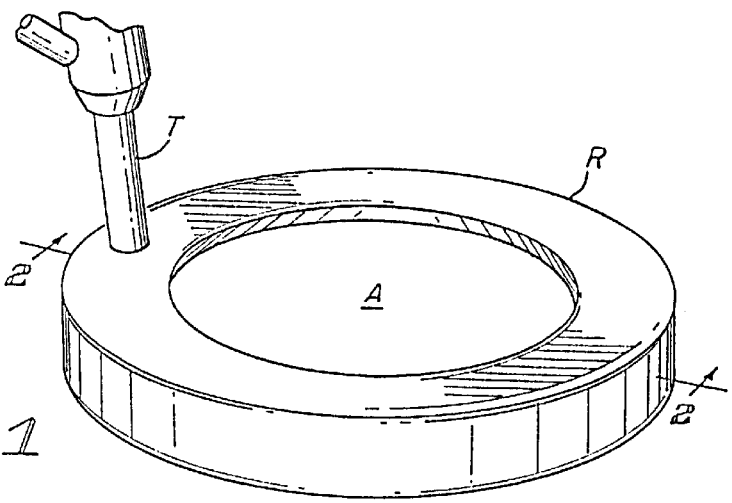
FIG. 1 is a perspective view of a common type of suction ring in communication with a hollow suction tube for applying a vacuum thereto.

Illustrated throughout the drawings, the present invention is directed generally towards a positioning assembly for improved retaining and positioning of a patient's eye, and preferably the cornea of the patient's eye which is to be cut during a surgical operation, and is generally indicated by reference numeral 10 in FIGS. 4 and 5. More specifically, the present invention is directed towards a suction enhancement assembly 40, for improving and preserving the vacuum seal which attaches a positioning element or segment to the patient's eye during surgery. It will be understood that although the positioning assembly 10 of the present invention is likely to be used in conjunction with a microkeratome device, the latter does not form a part of the present invention.

The positioning assembly 10 of the present invention is directed for use with and may comprise a positioning segment 20, also known as an eyeball positioning ring or positioning element, as illustrated in FIGS. 4 and 5, and preferably having an enclosed ring configuration so as to maximize its engagement with the eye. The positioning segment 20 is used to centrate the eye, that is, to retain, position and properly present the cornea of a patient's eyeball in a precise and aligned manner for surgery. Thus, the positioning segment 20 has a main body 22 which includes and defines a preferably enclosed aperture 25 therein. The aperture 25 is sized to receive and permit the cornea C, of the eye to pass therethrough so as to expose the cornea C, and a predetermined depth thereof, for cutting during surgery. Typically, the cornea C will be cut during surgery when a microkeratome with a cutting element is moved over the face of the positioning segment 20 and thus, over the exposed cornea C, which as is clear from the drawings, protrudes through the aperture 25. The positioning segment 20 is preferably formed of a rigid material and preferably, a metallic material. Ideally, however, the positioning segment 20 will be made of a high grade stainless steel, which enhances precision engagement with the eyeball, can be formed to have a smooth, safe and glare-retardant surface finish, and which provides for ease of sterilization.

As illustrated in the drawings, the main body 22 of positioning segment 20 is preferably defined by a generally circular shape about the aperture 25, although it will be appreciated that it could be formed to have another shape, such as a square, rectangular, hexagonal or other shape about the aperture 25, and still function for the intended purpose. In the preferred embodiment, the main body 22 of the positioning segment 20 comprises a retention plate 23, which includes the aperture 25 defined therein, and preferably a flange member 24 extending generally downwardly from the retention plate 23 and defining a generally open bottom side to the main body 22. Ideally, the flange member 24 is disposed in spaced apart, generally surrounding relation to the aperture 25 defined in the retention plate 23. Also in the preferred embodiment, the flange member 24 of main body 22 preferably includes a lower edge 27 which is structured and disposed to engage the portion of the eye about the cornea in a fluid impervious manner. Similarly, and as illustrated in FIGS. 4 and 5, the retention plate 23 preferably includes an interior rim 26 disposed in surrounding relation about the aperture 25, which is structured to engage the eye disposed therein, also in a fluid impervious manner. It will therefore be appreciated that upon the positioning segment 20 being disposed in engaging relation with the eye, that an effective, generally air-tight seal can be achieved about the eyeball between retention plate 23 and flange member 24.

The positioning assembly of the present invention is further directed for use with and may comprise a suctioning assembly 30 for attaching the positioning segment 20 to the eye on which surgery is to be performed. Preferably, the suctioning assembly 30 comprises a vacuum port 32 formed in the positioning segment 20 and a vacuum assembly (not shown) for providing a suction force. The vacuum assembly is structured to apply a suction force which is sufficient to attach the positioning segment 20 to the eyeball about the cornea, C, and cause the cornea to be urged upwardly and to protrude through the aperture 25 of the positioning segment 20, while not being so strong as to cause damage to the eyeball. It will be appreciated from the drawings that the vacuum port 32 formed in the positioning segment 20 is operably coupled to and in fluid flow communication with the vacuum assembly such that the suction force is applied therethrough. In a preferred embodiment, a tubular connection member 33 extends from the positioning segment 20 in fluid flow communication via an internal vacuum passage 35, with the vacuum port 32. Connection member 33 is adapted to be interconnected with a vacuum hose (not shown) which in turn may be connected to the vacuum assembly such that when the vacuum assembly is activated, the suction force is applied through the vacuum port 32. In the preferred embodiment, the vacuum port 32 is disposed at an undersurface 28 of positioning segment 20 either through retention plate 23 or flange member 24. Thus, the vacuum port 32 is disposed to provide a suction force, once the vacuum assembly is activated, to a point radially exterior of the aperture 25 and radially interior of the flange member 24, so as to form a seal about the cornea of the eye about to undergo surgery. It should be clear at this point that the structure of positioning segment 20, when accompanied by a suction force, acts to properly position and align the cornea C, for surgery and to generally maintain that position during surgery. Typically, a vacuum of about 25 inches of Hg at sea level will be used.

Figure 3A:
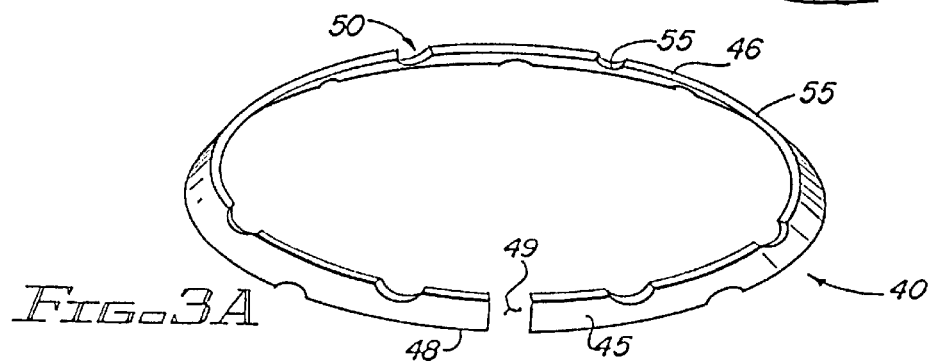
FIG. 3-A is a front view of the suction enhancement assembly of the present invention in a more preferred embodiment.
Figure 3B:
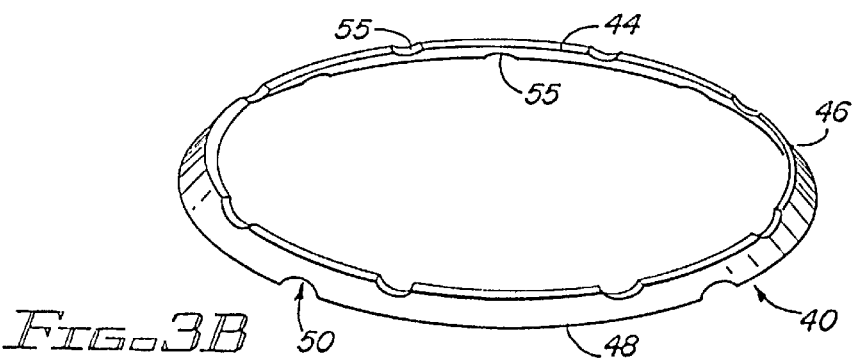

Referring now to FIGS. 3–5, the positioning assembly 10 of the present invention is seen to comprise suction enhancement assembly 40. The suction enhancement assembly 40 is structured to define a suction channel 42 and to at least partially maintain a flow-through integrity of the suction channel 42 upon generation of the suction force by the suctioning assembly 30. In an illustrated embodiment, the suction enhancement assembly 40 includes a suction enhancement member 44, which in the preferred embodiment comprises a segment 45 formed of a resilient material. The segment 45, which can be formed from a metallic material such as aluminum or stainless steel, and may include a hinge type structure so as to provide for a compression thereof, is preferably formed from a suitable plastic material to provide for ease of manufacture and economical disposal. Further, the resilient material segment 45 has a thickness of between generally about three-tenths (0.3 mm) of a millimeter to generally about five-tenths (0.5 mm) of a millimeter. Accordingly, the segment 45 will take up minimal space within the positioning segment 20 and consequently, will not misalign nor displace the positioning segment 20 relative to the eye.

As illustrated in FIGS. 4 and 5, the suction enhancement assembly 40, and in the illustrated embodiment the resilient material segment 45 of the suction enhancement assembly 40, is disposed within undersurface 28 of the positioning segment 20 and at least partially between the suctioning assembly 30 operably coupled to the positioning segment 20, and the portion of the eye surrounding the cornea to be cut. More specifically, the suction enhancement assembly 40 is structured to be defined between the vacuum port 32 of the positioning segment 20 and the eyeball to be cut during surgery. Furthermore, in the illustrated embodiment wherein the suction enhancement assembly 40 includes the resilient material segment 45, the segment 45 is structured to be disposed in fitted engagement within the positioning segment 20 about a region which is radially exterior of the aperture 25, and accordingly preferably radially interior of the flange member 24. In the illustrated embodiment, the segment 45 of the suction enhancement assembly 40 is additionally structured and disposed to engage the positioning segment 20 so as to define the suction channel 42 between the positioning segment 20 and the suction enhancement member 44, such as segment 45, itself. Preferably, the suction enhancement member 44 comprises a generally ring like configuration, as illustrated in FIG. 3-B, so as to extend substantially or completely about the aperture 25 defined in the main body of the positioning segment 20. By extending at least substantially about the aperture 25, the suction channel 42 defined by the suction enhancement member 44 also extends at least substantially about the eyeball.

The suction channel 42 is disposed in fluid flow communication with the suctioning assembly 30, and preferably, with the vacuum port 32 defined in the positioning segment 20. Further, the suction enhancement assembly 40 preferably includes at least one suction port 50 which extends into fluid flow communication with the suction channel 42. In the illustrated embodiment wherein the segment 45 helps define the suction channel 42, the segment 45 of the suction enhancement assembly 40 includes the suction port 50, which can be entirely and/or partially defined in the segment 45. In a preferred embodiment, however, the suction enhancement assembly 40 includes a plurality of suction ports 50, such as disposed throughout the length of the segment 45 so as to extend at least substantially about the eyeball. Accordingly, upon actuation of the vacuum assembly, a suction force is applied through the vacuum port 32, to the suction channel 42, and further, through the suction ports 50 so as to distribute the suction force more uniformly about the entire eyeball. As a result, the positioning segment 20 is likely to possess an improved ability to remain attached to the eyeball during surgery.

As indicated, the suction enhancement assembly 40 is additionally structured to maintain a flow-through-integrity of the suction channel 42 upon actuation of the vacuum assembly and the resulting attachment of the positioning segment 20 to the eyeball. Specifically, as the suction force is applied to the assembly, the inter-ocular pressure within the eye bulges so as to urge the eye upwardly and into the positioning segment 20. The suction enhancement assembly 40 is therefore, structured to resist collapse, and to thereby, maintain the flow-through-integrity of suction channel 42. To achieve this, the suction enhancement assembly 40, and in the illustrated embodiment segment 45, is formed to have an outward taper from the top edge 46 to the bottom edge 48 of the segment 45, as is perhaps best illustrated in FIGS. 3-A to 3-C. In the preferred embodiment, the outward taper of the segment 45 is between generally about thirty (30) and forty (40) degrees, and ideally, thirty-five (35) degrees between the top and bottom edges, 46, 48. Thus, the segment 45 is sized and structured to be angularly disposed in fitted engagement with the positioning segment 20 and includes a height dimension which is sufficient to extend between an undersurface 28 of the retention plate 23 and the flange member 24 of the positioning segment 20. More specifically, and illustrated in FIGS. 4–5, the top edge 46 of the segment 45 is structured to engage the retention plate 23, and the bottom edge 48 is structured to engage the flange member 24 of the positioning segment 20 so as to define the suction channel 42. As such, the material construction of the segment 45, along with engagement of its top and bottom edges 46, 48 with the positioning segment 20 prevents inward buckling as the cornea of the eye bulges upwardly and into position within aperture 25. In particular, even though the segment 45 is generally thin, it is seen that because of the small height dimension required to bridge the distance between flange member 24 and retention plate 23, it is nonetheless sufficient to resist inward buckling.

Figure 2:
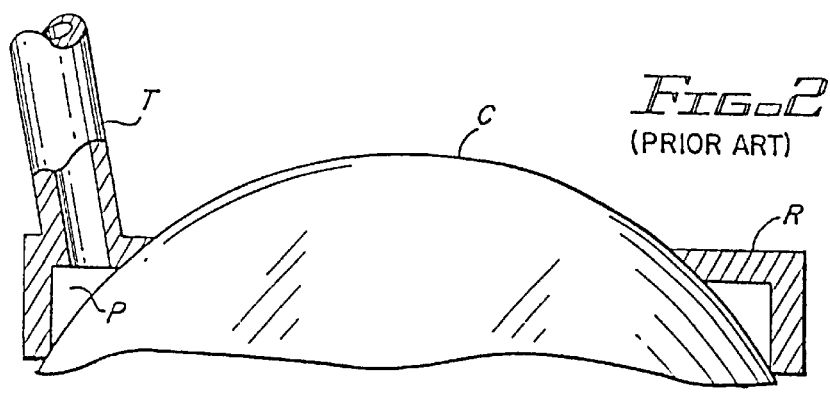
FIG. 2 is a partial cross sectional view of the suction ring device taken along the lines 2—2 illustrated in FIG. 1 and depicting an operative position about a cornea, C, with a suction force applied thereto.

In this regard, means to secure the segment 45 in removable engagement with the positioning segment 20 are preferably provided. As such, the resilient material segment 45 may be structured and disposed so as to frictionally engage the positioning segment 20, so as to be directed for use with available suction ring devices such as illustrated in FIGS. 1–2. In a more preferred embodiment, however, the flange member 24 of the positioning segment 20 includes an interiorly disposed ridge 29 formed thereon which may be said to further comprise the suction enhancement assembly and in the illustrated embodiment is sized and structured to receive the bottom edge 48 of the enhancement segment 45 supportably thereon, as illustrated in FIGS. 4 and 5. Specifically, the ridge 29, which may include an inwardly defined protrusion, is preferably defined by an interiorly disposed groove 29' that extends about the inner periphery of flange member 24. The groove 29' is sized and structured to receive the bottom edge 48 of the segment 45 therein. As such, a smooth and even contour is maintained at a portion of the positioning segment 20 which may engage the eye, and the segment 45 is recessed within the positioning segment 20 to further minimize a risk of displacing the eye relative to the positioning segment 20.

Also in the preferred embodiment, the suction ports 50 of the segment 45 have an inner diameter which, while sized to permit gentle gripping about the eyeball once a suction force has been activated, is not so large as to sacrifice or weaken the structural integrity of the suction enhancement member 44. Ideally, the suction ports 50 will comprise a plurality of indentations or cutout portions 55 formed along the top edge 46 and bottom edge 48 of the resilient material segment 45 so as to maintain an overall strength of the segment 45.

It will be appreciated from the foregoing that the suction enhancement assembly 40 of the present invention is structured and disposed to act as a barrier to significantly prevent blockage of the suction force being applied to the overall assembly 10. As has been described, when a suction force is applied to the eyeball during surgery, a mucous membrane about the eyeball, known as conjunctiva, may be drawn inwardly towards the vacuum port 32 of the positioning segment 20 and may result in the suction force being partially or completely blocked. In the preferred embodiment wherein the suction ports 50 are disposed throughout segment 45, which itself is disposed about the eyeball, the suction force is effectively distributed substantially three hundred and sixty degrees about the eyeball, such that a concentrated suction force which would tend to draw in the conjunctiva, is not present. Although the suction force is more evenly distributed, it is still sufficient to securely grasp the eye, but insufficient to draw in conjunctiva. Thus, the segment 45 is structured and disposed to prevent both partial and complete occlusion of the suction force applied via the vacuum port 32. In addition, however, the suction enhancement assembly 40 acts as a barrier to limit, if not prevent altogether, the entry of mucous from the eye into the suction channel 42 and the internal vacuum passages 32, 35 of the positioning segment 20. This factor also helps to ensure that the suction force will not become occluded eventually by the accumulation of mucous in the internal vacuum passages of the positioning segment.

In the preferred embodiment, the segment 45 of the suction enhancement assembly 40 is structured and disposed to removably engage the positioning segment 20 so as to facilitate cleaning of the positioning segment 20 for subsequent use on another patient. As an initial matter, the suction enhancement assembly 40 of the present invention maintains the positioning segment 20 in a cleaner condition than is presently known in the art because mucous from the eye is substantially prevented from entering into the suction channel 42 and internal vacuum passages of the positioning segment 20. On the other hand, at least part of the suction enhancement assembly 40 is likely to have contacted the eye's mucous tissue during surgery. To avoid additional cleaning, in the preferred embodiment, wherein the suction enhancement assembly 40 includes the resilient material segment 45, the segment 45 is structured and disposed to be removable from the positioning segment 20, whereupon it can be safely and easily disposed of. It will be appreciated that by removing the resilient material segment 45 from the positioning segment 20, the under surfaces of the positioning segment 20 is easily accessible for cleaning and sterilization. Additionally, the resilient material segment 45 is preferably formed of a suitably resilient plastic material that is sufficiently flexible to be temporarily compressed, so as to facilitate introduction and removal of the segment 45 into and out of engagement with the positioning segment 20, with minimal risk of causing damage to the positioning segment 20. In a more preferred embodiment, resilient material segment 45 may be structured to include a gap 49 defined therein which permits a diameter of the generally circular shape formed by the segment 45 to be temporarily compressed during introduction and removal of the segment 45 from the positioning segment 20. In this embodiment, when the segment 45 is disposed in an operative position within the positioning segment 20, the gap 49 may itself define a suction port 50 in that the segment 45 will generally not completely encircle the eyeball, and may in fact, only extend partially thereabout. Of course, while segment 45 is sufficiently flexible for temporary compression, it is also sufficiently rigid so as to not itself be sucked out of position, and further, so as to have an elastic memory sufficient to return the segment 45 towards its normal, at rest position, and thereby, maintain segment 45 securely in place within the positioning segment 20. In this regard, it should be understood that segment 45 may be formed to include a biasing force to be exerted by the segment 45 on the flange member 24 which is sufficient to retain the segment 45 in fitted engagement within the flange member 24. Alternatively, the segment 45 does not necessarily have to include a biasing force as in one embodiment, since interiorly disposed ridge 27 on flange member 24 may be sufficient to retain segment 45 in fitted engagement with positioning segment 20.

Since many modifications, variations and changes in detail can be made to the described preferred embodiment of the invention, it is intended that all matters in the foregoing description and shown in the accompanying drawings be interpreted in the illustrative and not in a limiting sense. Thus, the scope of the invention should be determined by the appended claims and their legal equivalents.

Now that the invention has been described,

What is claimed is:

1. A positioning assembly for retaining and positioning a patient's eye during a surgical operation, said assembly comprising:
   a) a positioning element at least partially structured to receive and expose abortion of the eye;
   b) a suctioning assembly structured to at least temporarily dispose said positioning element on the eye;
   c) a suction enhancement assembly structured to promote attachment of said positioning element to the patient's eye;
   d) said suctioning enhancement assembly defining a suction channel disposed in operative communication with said suctioning assembly and the patient's eye such that a suction force generated by said suctioning assembly is at least partially applied through said suction channel to the patient's eye; and
   e) said suction enhancement assembly structured to at least partially maintain a flow-through integrity of said suction channel upon generation of the suction force by said suctioning assembly;
   f) said suction enhancement assembly including a material segment angularly disposed within said positioning element; and
   g) said material segment being removably disposed in said positioning element.

2. A positioning assembly as recited in claim 1 wherein said segment is disposed at least partially between said suctioning assembly and the portion of the patient's eye.

3. A positioning assembly as recited in claim 2 wherein said suction enhancement assembly further comprises at least one suction port disposed in fluid flow communication between said suction channel and the eye.

4. A positioning assembly as recited in claim 3 wherein said suction port is defined by said segment.

5. A positioning assembly as recited in claim 4 comprising a plurality of said suction ports.

6. A positioning assembly as recited in claim 1 wherein said segment is formed at least partially from a flexible material.

7. A positioning assembly as recited in claim 1 wherein said positioning element at least partially defines said suction channel.

8. A positioning assembly as recited in claim 7 further comprising an interior ridge defined in said positioning element.

9. A positioning assembly as recited in claim 8 wherein said suction enhancement assembly further comprises a material segment structured to further define said suction channel and maintains said flow-through integrity thereof.

10. A positioning assembly as recited in claim 9 wherein a bottom edge of said segment is structured to at least partially engage said interior ridge, said interior ridge structured to at least partially maintain said segment angularly disposed in removable, fitted engagement within said positioning element.

11. A positioning assembly as recited in claim 10 wherein said suction enhancement assembly further comprises at least one suction port defined by said segment and disposed in fluid flow communication between said suction channel and the eye.

12. A positioning assembly as recited in claim 7 further comprising an interior groove defined in said positioning element.

13. A positioning assembly as recited in claim 12 wherein said suction enhancement assembly further comprises a material segment structured to further define said suction channel.

14. A positioning assembly as recited in claim 13 wherein a bottom edge of said segment is at least partially received by said interior groove, said interior groove structured to at least partially maintain said segment angularly disposed in removable, fitted engagement within said positioning segment.

15. A positioning assembly as recited in claim 14 wherein said suction enhancement assembly further comprises at least one suction port defined by said segment and disposed in fluid flow communication between said suction channel and the eye.

16. A positioning assembly for retaining and positioning a patient's eye during a surgical operation, said assembly comprising:
   a) a positioning element at least partially structured to receive and expose a portion of the eye;
   b) a suctioning assembly structured to at least temporarily dispose said positioning element on the eye;
   c) a suction enhancement assembly structured to promote attachment of said positioning element to the patient's eye;
   d) said suctioning enhancement assembly defining a suction channel disposed in operative communication with said suctioning assembly and the patient's eye such that a suction force generated by said suctioning assembly is at least partially applied through said suction channel to the patient's eye;
   e) said suction enhancement assembly structured to at least partially maintain a flow-through integrity of said suction channel upon generation of the suction force by said suctioning assembly; and
   f) said suction enhancement assembly further including at least one suction port disposed in fluid flow communication between said suction channel and the eye.

17. A positioning assembly for retaining and positioning a patient's eye during a surgical operation, said assembly comprising:
   a) a positioning element at least partially structured to receive and expose a portion of the eye;

b) a suctioning assembly structured to at least temporarily dispose said positioning element on the eye;
c) a suction enhancement assembly structured to promote attachment of said positioning element to the patient's eye;
d) said suctioning enhancement assembly defining a suction channel disposed in operative communication with said suctioning assembly and the patient's eye such that a suction force generated by said suctioning assembly is at least partially applied through said suction channel to the patient's eye;
e) said suction enhancement assembly structured to at least partially maintain a flow-through integrity of said suction channel upon generation of the suction force by said suctioning assembly; and
f) said positioning element at least partially defining said suction channel; and
g) an interior ridge defined in said positioning element.

18. A positioning assembly for retaining and positioning a patient's eye during a surgical operation, said assembly comprising:

a) a positioning element at least partially structured to receive and expose a portion of the eye;
b) a suctioning assembly structured to at least temporarily dispose said positioning element on the eye;
c) a suction enhancement assembly structured to promote attachment of said positioning element to the patient's eye;
d) said suctioning enhancement assembly defining a suction channel disposed in operative communication with said suctioning assembly and the patient's eye such that a suction force generated by said suctioning assembly is at least partially applied through said suction channel to the patient's eye;
e) said suction enhancement assembly structured to at least partially maintain a flow-through integrity of said suction channel upon generation of the suction force by said suctioning assembly; and
f) said positioning element at least partially defining said suction channel; and
g) an interior groove defined in said positioning element.

* * * * *